United States Patent [19]
Grammatikakis et al.

[11] Patent Number: 6,066,723
[45] Date of Patent: May 23, 2000

[54] NUCLEIC ACID ENCODING VERTEBRATE CDC37

[75] Inventors: Nicholas Grammatikakis; Aliki Grammatikakis, both of Brighton; Bryan P. Toole, Watertown; Brent Cochran, Newton, all of Mass.

[73] Assignee: Trustees of Tufts College, Medford, Mass.

[21] Appl. No.: 08/675,885

[22] Filed: Jul. 5, 1996

[51] Int. Cl.[7] .................................................. C07H 21/04
[52] U.S. Cl. .......................................... 536/23.5; 536/23.1
[58] Field of Search ............................. 435/240.2, 370.1, 435/252.3, 325; 536/23.1, 24.22, 23.5

[56] References Cited

U.S. PATENT DOCUMENTS 5,756,671  5/1998  Gyuris et al. ............................ 530/350

FOREIGN PATENT DOCUMENTS

WO 95/33819  12/1995  WIPO .

OTHER PUBLICATIONS

Grammatikakis et al., Poster Abstract, Keystone Symposia on the Extracellular Matrix, Breckenridge, CO (Mar., 1993).
Qin Yu et al., *Developmental Dynamics* 193: 145–151 (1992).
Ozaki et al., *DNA Cell Biol.* 14: 1017–1023 (1995).
Cutforth and Rubin, *Cell* 77: 1027–1036 (1994).
Grammatikakis et al., *J. Biol. Chem. 270:* 16198–16205 (1995).
Stepanova et al., *Genes and Devel. 10:* 1491–1502 (1996).

*Primary Examiner*—James Ketter
*Assistant Examiner*—Irem Yucel
*Attorney, Agent, or Firm*—Kevin M. Farrell

[57] ABSTRACT

Disclosed are substantially pure nucleic acid sequences encoding vertebrate cdc37. The protein encoded by this nucleic acid is characterized by the ability to bind specifically to mammalian proteins selected from the group consisting of cdk4, cyclin D, cdk2, Rb, hsp90, hsp60, hsp70, Raf-1, MEK-1, SAPK, MAPK, ERK1, P13-K and the src family of tyrosine kinases. In addition, the protein is further characterized by the ability to bind glycosaminoglycan. Also disclosed are diagnostic and therapeutic applications based on the isolation of the nucleic acid sequences.

8 Claims, No Drawings

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 823 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 64..801

(xi) SEQUENCE DESCRIPTION: SEQ ID NO:1:

```
AGGGAGAGGC TGCAGGCGGA GGCGCAGCAG CTGCGCCACG AGGAGAGGAA CTGGGAGAGC      60

AAA ATG GAG GAG CTG CGC AAG AAG GAG AAG AAT ATG CCC TGG AAC GTC     108
    Met Glu Glu Leu Arg Lys Lys Glu Lys Asn Met Pro Trp Asn Val
    1               5                  10                  15

GAC ACG CTG AGC AAG GAC GGC TTC AGC AAG AGC GTT TTC AAC GTG AAG     156
Asp Thr Leu Ser Lys Asp Gly Phe Ser Lys Ser Val Phe Asn Val Lys
                20                  25                  30

GCA GAG GAG AAG GAG GAG ACG GAG GAG CAG AAG GAG CAG AAG CAC AAA     204
Ala Glu Glu Lys Glu Glu Thr Glu Glu Gln Lys Glu Gln Lys His Lys
                35                  40                  45

ACC TTC GTG GAG CGC CAC GAG AAG CAG ATC AAG CAC TTT GGC ATG CTG     252
Thr Phe Val Glu Arg His Glu Lys Gln Ile Lys His Phe Gly Met Leu
            50                  55                  60

CGG CGC TGG GAC GAC AGC CAG AAG TAC CTC TCG GAC AAC CCA CAC CTC     300
Arg Arg Trp Asp Asp Ser Gln Lys Tyr Leu Ser Asp Asn Pro His Leu
        65                  70                  75

GTT TGC GAG GAG ACT GCT AAT TAC CTG GTC ATC TGG TGC ATC GAC CTG     348
Val Cys Glu Glu Thr Ala Asn Tyr Leu Val Ile Trp Cys Ile Asp Leu
80                  85                  90                  95

GAG GTG GAG GAG AAG CAG GCT CTG ATG GAG CAG GTC GCC CAC CAG ACC     396
Glu Val Glu Glu Lys Gln Ala Leu Met Glu Gln Val Ala His Gln Thr
                100                 105                 110

ATC GTC ATG CAG TTC ATC CTG GAG TTG GCC AAG AGC CTC AAG GTG GAT     444
Ile Val Met Gln Phe Ile Leu Glu Leu Ala Lys Ser Leu Lys Val Asp
            115                 120                 125

CCC CGC GCG TGC TTC CGT CAG TTC TTC ACC AAA ATC AAG ACC GCC GAC     492
Pro Arg Ala Cys Phe Arg Gln Phe Phe Thr Lys Ile Lys Thr Ala Asp
        130                 135                 140

CAG CAG TAC ATG GAG GGC TTC AAC GAT GAG TTG GAG GCC TTC AAG GAG     540
Gln Gln Tyr Met Glu Gly Phe Asn Asp Glu Leu Glu Ala Phe Lys Glu
145                 150                 155

CGC GTG CGC GGC CGG GCC AAG GCG CGC ATC GAG AGG GCC ATG CGG GAG     588
Arg Val Arg Gly Arg Ala Lys Ala Arg Ile Glu Arg Ala Met Arg Glu
160                 165                 170                 175

TAC GAG GAG GAG GAG CGG CAG AAG CGC CTG GGG CCC GGC GGC CTC GAC     636
Tyr Glu Glu Glu Glu Arg Gln Lys Arg Leu Gly Pro Gly Gly Leu Asp
                180                 185                 190

CCC GTC GAC GTC TAC GAG TCC CTC CCA CCC GAG CTG CAG AAA TGC TTT     684
Pro Val Asp Val Tyr Glu Ser Leu Pro Pro Glu Leu Gln Lys Cys Phe
            195                 200                 205

GAC GCC AAA GAC GTG CAG ATG CTG CAG GAC ACC ATC AGC CGA ATG GAC     732
Asp Ala Lys Asp Val Gln Met Leu Gln Asp Thr Ile Ser Arg Met Asp
```

-continued

```

Asp Ala Lys Asp Val Gln Met Leu Gln Asp Thr Ile Ser Arg Met Asp
        210                 215                 220

CCC ACT GAG GCC AAA TAC CAC ATG CAG CGC TGC ATC GAT TCG GGG CTG        780
Pro Thr Glu Ala Lys Tyr His Met Gln Arg Cys Ile Asp Ser Gly Leu
    225                 230                 235

TGG GTC CCA ACT CAG CAC CAA TAAAGTGATG AAGCATGGAA AA                    823
Trp Val Pro Thr Gln His Gln
240             245
```

(2) INFORMATION FOR SEQ ID NO:2:

(i) SEQUENCE CHARACTERISTICS:
        (A) LENGTH: 246 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Glu Leu Arg Lys Lys Glu Lys Asn Met Pro Trp Asn Val Asp
 1               5                  10                  15

Thr Leu Ser Lys Asp Gly Phe Ser Lys Ser Val Phe Asn Val Lys Ala
             20                  25                  30

Glu Glu Lys Glu Glu Thr Glu Glu Gln Lys Glu Gln Lys His Lys Thr
         35                  40                  45

Phe Val Glu Arg His Glu Lys Gln Ile Lys His Phe Gly Met Leu Arg
     50                  55                  60

Arg Trp Asp Asp Ser Gln Lys Tyr Leu Ser Asp Asn Pro His Leu Val
 65                  70                  75                  80

Cys Glu Glu Thr Ala Asn Tyr Leu Val Ile Trp Cys Ile Asp Leu Glu
                 85                  90                  95

Val Glu Glu Lys Gln Ala Leu Met Glu Gln Val Ala His Gln Thr Ile
            100                 105                 110

Val Met Gln Phe Ile Leu Glu Leu Ala Lys Ser Leu Lys Val Asp Pro
        115                 120                 125

Arg Ala Cys Phe Arg Gln Phe Phe Thr Lys Ile Lys Thr Ala Asp Gln
    130                 135                 140

Gln Tyr Met Glu Gly Phe Asn Asp Glu Leu Glu Ala Phe Lys Glu Arg
145                 150                 155                 160

Val Arg Gly Arg Ala Lys Ala Arg Ile Glu Arg Ala Met Arg Glu Tyr
                165                 170                 175

Glu Glu Glu Glu Arg Gln Lys Arg Leu Gly Pro Gly Gly Leu Asp Pro
            180                 185                 190

Val Asp Val Tyr Glu Ser Leu Pro Pro Glu Leu Gln Lys Cys Phe Asp
        195                 200                 205

Ala Lys Asp Val Gln Met Leu Gln Asp Thr Ile Ser Arg Met Asp Pro
    210                 215                 220

Thr Glu Ala Lys Tyr His Met Gln Arg Cys Ile Asp Ser Gly Leu Trp
225                 230                 235                 240

Val Pro Thr Gln His Gln
            245
```

(2) INFORMATION FOR SEQ ID NO:3:

(i) SEQUENCE CHARACTERISTICS:
        (A) LENGTH: 974 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

```
GTTGTACAGA GATGCAGTGG ATGCCCTGTT GTTGGAGAAA CTCACGGTCA GGCTGGACGG      60

GCCTCTGAGC ACCGTGATGG AGCTGTAGGT GTCCTTATTC ATTGCAGGGG AGTTGGACTA     120

GATGACCTTT AAGGGTCCCT TCCAACTCGA ACAATTTTAT GTTAATATAG ATAATCAGAT     180

TAAATAATAC ATAGCTGTAT ATACACTAAT ATCTGTATGT TAACCAGAAT ATGAAGGAGC     240

TAATAAACAG TAATTTTCTG GTGGTTATAA AAAGTCAGGT ACTACAAGAA TTTAAAAAAG     300

GAGAAATGCT TAATAATTAG ATTAGCAAGA AAAATCTTTT TAATACTGTC AGAATCAGGA     360

GAACTCTGCT ATCTTATAAA CCTGAAAGCA CAACTGATAA TGCAGTTATC AGTTGCAGAG     420

CTAGAGATGA TGCACGAGAG TAATCCAGTA TGTAGGACTG CACGTTTTTA GTTGTCTGCT     480

CTGTTTCTGT GCAGTAATTT GTACCAAAGA TGGTGAGATG ATTGGACAGC ACTTCAAATC     540

TTCTCGTAGT AAAATATGAA GCAGATTTAC TATATTGTTG TTATATTGGT GTACAAATGA     600

AAATGCAGTG CACTGCAACC ATTGTCCACT ACTGCATATG AAACATGGCA TAGTGGAATA     660

TCCCAAGAGC TAAATTAGCC TGCTGAAGAG CCTTTCTCTT TCATCAGACT TATTTTATCA     720

GTGGACACCT GACTATCCGA GAAGCACAGT ATGTGTTTTT TTTTTTTTTC AGTTAGCCAA     780

AAGCCCCAAT TCAAACGTTC AGTTGGGTAG TTTTTATAAT GTTTTCAAAG GCAGTCTAGT     840

GTTTTTATGT TGGAATACTG ACTTGTGCAT GTTGATGATG ATGACTTGTG CATGTTGATG     900

ATGATGACTG TTGTACACCC TGTCTTTTTT GTATTTTATG TTTGAAAAGA AATTAAAGAA     960

GTATATCTTT AAAA                                                       974
```

(2) INFORMATION FOR SEQ ID NO:4:

(i) SEQUENCE CHARACTERISTICS:
        (A) LENGTH: 1847 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 48..704

(xi) SEQUENCE DESCRIPTION: SEQ ID NO:4:

```
CGCCGTCGCC GCCACCCGAG CCGGAGCGGG CTGGGCCCCA AGGCAAG ATG GTG GAC        56
                                                    Met Val Asp
                                                      1

TAC AGC GTG TGG GAC CAC ATT GAG GTG TCT GAT GAT GAA GAC GAG ACG       104
Tyr Ser Val Trp Asp His Ile Glu Val Ser Asp Asp Glu Asp Glu Thr
      5                  10                  15

CAC CCC AAC ATC GAC ACG GCC AGT CTC TTC CGC TGG CGG CAT CAG GCC       152
His Pro Asn Ile Asp Thr Ala Ser Leu Phe Arg Trp Arg His Gln Ala
 20                  25                  30                  35

CGG GTG GAA CGC ATG GAG CAG TTC CAG AAG GAG AAG GAG GAA CTG GAC       200
Arg Val Glu Arg Met Glu Gln Phe Gln Lys Glu Lys Glu Glu Leu Asp
                 40                  45                  50

AGG GGC TGC CGC GAG TGC AAG CGC AAG GTG GCC GAG TGC CAG AGG AAA       248
Arg Gly Cys Arg Glu Cys Lys Arg Lys Val Ala Glu Cys Gln Arg Lys
             55                  60                  65

CTG AAG GAG CTG GAG GTG GCC GAG GGC GGC AAG GCA GAG CTG GAG CGC       296
Leu Lys Glu Leu Glu Val Ala Glu Gly Gly Lys Ala Glu Leu Glu Arg
         70                  75                  80
```

| | | |
|---|---|---|
| CTG CAG GCC GAG GCA CAG CAG CTG CGC AAG GAG GAG CGG AGC TGG GAG<br>Leu Gln Ala Glu Ala Gln Gln Leu Arg Lys Glu Glu Arg Ser Trp Glu<br>85                        90                             95 | 344 |
| CAG AAG CTG GAG GAG ATG CGC AAG AAG GAG AAG AGC ATG CCC TGG AAC<br>Gln Lys Leu Glu Glu Met Arg Lys Lys Glu Lys Ser Met Pro Trp Asn<br>100                     105                   110                   115 | 392 |
| GTG GAC ACG CTC AGC AAA GAC GGC TTC AGC AAG GCC CAT GCC CAC GCT<br>Val Asp Thr Leu Ser Lys Asp Gly Phe Ser Lys Ala His Ala His Ala<br>                 120                   125                   130 | 440 |
| CCC GCC ACC TTG ATG CTC ATG GCT TCG TCA CCA CCT CCG CCG TGG ATG<br>Pro Ala Thr Leu Met Leu Met Ala Ser Ser Pro Pro Pro Pro Trp Met<br>            135                   140                   145 | 488 |
| GGA TGG GCG CTG CGA CCA CGG CCC GCC CGG CCG CGC TCG AGG CGC TCC<br>Gly Trp Ala Leu Arg Pro Arg Pro Ala Arg Pro Arg Ser Arg Arg Ser<br>         150                   155                   160 | 536 |
| GCA GCC TTG CCC CAG CCC ACT CCC CCT CTC ACC CTA CCA CAG AGC ATG<br>Ala Ala Leu Pro Gln Pro Thr Pro Pro Leu Thr Leu Pro Gln Ser Met<br>165                     170                   175 | 584 |
| GTA AAT ACC AAG CCC GAG AAG ACG GAG GAG GAC TCA GAG GAG GTG AGG<br>Val Asn Thr Lys Pro Glu Lys Thr Glu Glu Asp Ser Glu Glu Val Arg<br>180                     185                   190                   195 | 632 |
| GAG CAG AAA CAC AAG ACC TTC GTG GAA AAA TAC GAG AAA CAG ATC AAG<br>Glu Gln Lys His Lys Thr Phe Val Glu Lys Tyr Glu Lys Gln Ile Lys<br>                 200                   205                   210 | 680 |
| CAC TTT GGT GAG TGG GGC TTG TGAGTTATGG GGGCAAGGT CGAGGCAGGC<br>His Phe Gly Glu Trp Gly Leu<br>                 215 | 731 |
| CCTTTGCCTC CAGGGCCCTC CAGCACCTTG CCAGCATCTT CCCACAGGCA TGCTTCGCCG | 791 |
| CTGGGATGAC AGCCAAAAGT ACCTGTCAGA CAACGTCCTC CTGGTGTGCG AGGAGACAGC | 851 |
| CAATTACCTG GTCATTTGGT GCATTGACCT AGAGGTGGAG GAGAAATGTG CACTCATGGA | 911 |
| GCAGGAGGCC CACCAGACAA TCGTCATGCA ATTTATCCTG GAGCTGGCCA AGAGCCTAAA | 971 |
| GGTGGACCCC CGGGCCTGCT TCCGGCAGTT CTTCACTAAG ATTAAGACAG CCGATCGCCA | 1031 |
| GTACATGGAG GGCTTCAACG ACGAGCTGGA AGCCTTCAAG GAGCGTGTGC GGGGCCGTGC | 1091 |
| CAAGCTGCGC ATCGAGAAGG CCATGAAGGA GTACGAGGAG GAGGAGCGCA AGAAGCGGCT | 1151 |
| CGGCCCCGGC GGCCTGGACC CCGTCGAGGT CTACGAGTCC CTCCCTGAGG AACTCCAGAA | 1211 |
| GTGCTTCGAT GTGAAGGACG TGCAGATGCT GCAGGACGCC ATCAGCAAGA TGGACCCCAC | 1271 |
| CGACGCAAAG TACCACATGC AGCGCTGCAT TGACTCTGGC CTCTGGGTCC CCAACTCTAA | 1331 |
| GGCCAGCGAG GCCAAGGAGG GAGAGGAGGC AGGTCCTGGG GACCCATTAC TGGAAGCTGT | 1391 |
| TCCCAAGACG GGCGATGAGA AGGATGTCAG TGTGTGACCT GCCCCAGCTA CCACCGCCAC | 1451 |
| CTGCTTCCAG GCCCCTATGT GCCCCTTTTC AGAAAACAGA TAGATGCCAT CTCGCCCGCT | 1511 |
| CCTGACTTCC TCTACTTGCG CTGCTCGGCC CAGCCTGGGG GCCCGCCCAG CCCTCCCTGG | 1571 |
| CCTCTCCACT GTCTCCACTC TCCAGCGCCC ATTCAAGTCT CTGCTTTGAG TCAAGGGGCT | 1631 |
| TCACTGCCTG CAGCCCCCCA TCAGCATTAT GCCAAAGGCC CGGGGGTCCG GGAAGGGCA | 1691 |
| GAGGTCACCA GGCTGGTCTA CCAGGTAGTT GGGGAGGGTC CCCAGCCAAG GGGCCGGCTC | 1751 |
| TCGTCACTGG GCTCTGTTTT CACTGTTCGT CTGCTGTCTG TGTCTTCTAT TTGGCAAACA | 1811 |
| GCAATGATCT TCCAATAAAA GATTTCAGAT GCTAAA | 1847 |

(2) INFORMATION FOR SEQ ID NO:5:

(i) SEQUENCE CHARACTERISTICS:

(A) LENGTH: 218 amino acids
        (B) TYPE: amino acid
        (D) TOPOLOGY: linear (ii) MOLECULE TYPE: protein (xi) SEQUENCE DESCRIPTION: SEQ ID NO:5:

Met Val Asp Tyr Ser Val Trp Asp His Ile Glu Val Ser Asp Asp Glu
 1               5                  10                  15

Asp Glu Thr His Pro Asn Ile Asp Thr Ala Ser Leu Phe Arg Trp Arg
             20                  25                  30

His Gln Ala Arg Val Glu Arg Met Glu Gln Phe Gln Lys Glu Lys Glu
         35                  40                  45

Glu Leu Asp Arg Gly Cys Arg Glu Cys Lys Arg Lys Val Ala Glu Cys
 50                  55                  60

Gln Arg Lys Leu Lys Glu Leu Glu Val Ala Glu Gly Lys Ala Glu
 65              70                  75                  80

Leu Glu Arg Leu Gln Ala Glu Ala Gln Gln Leu Arg Lys Glu Glu Arg
                 85                  90                  95

Ser Trp Glu Gln Lys Leu Glu Glu Met Arg Lys Lys Glu Lys Ser Met
             100                 105                 110

Pro Trp Asn Val Asp Thr Leu Ser Lys Asp Gly Phe Ser Lys Ala His
         115                 120                 125

Ala His Ala Pro Ala Thr Leu Met Leu Met Ala Ser Ser Pro Pro Pro
130                 135                 140

Pro Trp Met Gly Trp Ala Leu Arg Pro Arg Pro Ala Arg Pro Arg Ser
145                 150                 155                 160

Arg Arg Ser Ala Ala Leu Pro Gln Pro Thr Pro Pro Leu Thr Leu Pro
                 165                 170                 175

Gln Ser Met Val Asn Thr Lys Pro Glu Lys Thr Glu Glu Asp Ser Glu
             180                 185                 190

Glu Val Arg Glu Gln Lys His Lys Thr Phe Val Glu Lys Tyr Glu Lys
         195                 200                 205

Gln Ile Lys His Phe Gly Glu Trp Gly Leu
    210                 215

(2) INFORMATION FOR SEQ ID NO:6:

(i) SEQUENCE CHARACTERISTICS:
        (A) LENGTH: 1603 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 48..1184

(xi) SEQUENCE DESCRIPTION: SEQ ID NO:6:

CGCCGTCGCC GCCACCCGAG CCGGAGCGGG CTGGGCCCCA AGGCAAG ATG GTG GAC        56
                                                   Met Val Asp
                                                    1

TAC AGC GTG TGG GAC CAC ATT GAG GTG TCT GAT GAT GAA GAC GAG ACG       104
Tyr Ser Val Trp Asp His Ile Glu Val Ser Asp Asp Glu Asp Glu Thr
     5                  10                  15

CAC CCC AAC ATC GAC ACG GCC AGT CTC TTC CGC TGG CGG CAT CAG GCC       152
His Pro Asn Ile Asp Thr Ala Ser Leu Phe Arg Trp Arg His Gln Ala
         20                  25                  30                  35

-continued

| | |
|---|---|
| CGG GTG AAA CGC ATG GAG CAG TTC CAG AAG GAG AAG GAG GAA CTG GAC<br>Arg Val Glu Arg Met Glu Gln Phe Gln Lys Glu Lys Glu Glu Leu Asp<br>                40                            45                          50 | 200 |
| AGG GGC TGC CGC GAG TGC AAG CGC AAG GTG GCC GAG TGC CAG AGG AAA<br>Arg Gly Cys Arg Glu Cys Lys Arg Lys Val Ala Glu Cys Gln Arg Lys<br>              55                            60                          65 | 248 |
| CTG AAG GAG CTG GAG GTG GCC GAG GGC GGC AAG GCA GAG CTG GAG CGC<br>Leu Lys Glu Leu Glu Val Ala Glu Gly Gly Lys Ala Glu Leu Glu Arg<br>              70                            75                          80 | 296 |
| CTG CAG GCC GAG GCA CAG CAG CTG CGC AAG GAG GAG CGG AGC TGG GAG<br>Leu Gln Ala Glu Ala Gln Gln Leu Arg Lys Glu Glu Arg Ser Trp Glu<br>              85                            90                          95 | 344 |
| CAG AAG CTG GAG GAG ATG CGC AAG AAG GAG AAG AGC ATG CCC TGG AAC<br>Gln Lys Leu Glu Glu Met Arg Lys Lys Glu Lys Ser Met Pro Trp Asn<br>100                      105                      110                      115 | 392 |
| GTG GAC ACG CTC AGC AAA GAC GGC TTC AGC AAG AGC ATG GTA AAT ACC<br>Val Asp Thr Leu Ser Lys Asp Gly Phe Ser Lys Ser Met Val Asn Thr<br>              120                          125                          130 | 440 |
| AAG CCC GAG AAG ACG GAG GAG GAC TCA GAG GAG GTG AGG GAG CAG AAA<br>Lys Pro Glu Lys Thr Glu Glu Asp Ser Glu Glu Val Arg Glu Gln Lys<br>              135                          140                          145 | 488 |
| CAC AAG ACC TTC GTG GAA AAA TAC GAG AAA CAG ATC AAG CAC TTT GGC<br>His Lys Thr Phe Val Glu Lys Tyr Glu Lys Gln Ile Lys His Phe Gly<br>              150                          155                          160 | 536 |
| ATG CTT CGC CGC TGG GAT GAC AGC CAA AAG TAC CTG TCA GAC AAC GTC<br>Met Leu Arg Arg Trp Asp Asp Ser Gln Lys Tyr Leu Ser Asp Asn Val<br>              165                          170                          175 | 584 |
| CTC CTG GTG TGC GAG GAG ACA GCC AAT TAC CTG GTC ATT TGG TGC ATT<br>Leu Leu Val Cys Glu Glu Thr Ala Asn Tyr Leu Val Ile Trp Cys Ile<br>180                      185                      190                      195 | 632 |
| GAC CTA GAG GTG GAG GAG AAA TGT GCA CTC ATG GAG CAG GAG GCC CAC<br>Asp Leu Glu Val Glu Glu Lys Cys Ala Leu Met Glu Gln Glu Ala His<br>              200                          205                          210 | 680 |
| CAG ACA ATC GTC ATG CAA TTT ATC CTG GAG CTG GCC AAG AGC CTA AAG<br>Gln Thr Ile Val Met Gln Phe Ile Leu Glu Leu Ala Lys Ser Leu Lys<br>              215                          220                          225 | 728 |
| GTG GAC CCC CGG GCC TGC TTC CGG CAG TTC TTC ACT AAG ATT AAG ACA<br>Val Asp Pro Arg Ala Cys Phe Arg Gln Phe Phe Thr Lys Ile Lys Thr<br>              230                          235                          240 | 776 |
| GCC GAT CGC CAG TAC ATG GAG GGC TTC AAC GAC GAG CTG GAA GCC TTC<br>Ala Asp Arg Gln Tyr Met Glu Gly Phe Asn Asp Glu Leu Glu Ala Phe<br>              245                          250                          255 | 824 |
| AAG GAG CGT GTG CGG GGC CGT GCC AAG CTG CGC ATC GAG AAG GCC ATG<br>Lys Glu Arg Val Arg Gly Arg Ala Lys Leu Arg Ile Glu Lys Ala Met<br>260                      265                      270                      275 | 872 |
| AAG GAG TAC GAG GAG GAG GAG CGC AAG AAG CGG CTC GGC CCC GGC GGC<br>Lys Glu Tyr Glu Glu Glu Glu Arg Lys Lys Arg Leu Gly Pro Gly Gly<br>              280                          285                          290 | 920 |
| CTG GAC CCC GTC GAG GTC TAC GAG TCC CTC CCT GAG GAA CTC CAG AAG<br>Leu Asp Pro Val Glu Val Tyr Glu Ser Leu Pro Glu Glu Leu Gln Lys<br>              295                          300                          305 | 968 |
| TGC TTC GAT GTG AAG GAC GTG CAG ATG CTG CAG GAC GCC ATC AGC AAG<br>Cys Phe Asp Val Lys Asp Val Gln Met Leu Gln Asp Ala Ile Ser Lys<br>              310                          315                          320 | 1016 |
| ATG GAC CCC ACC GAC GCA AAG TAC CAC ATG CAG CGC TGC ATT GAC TCT<br>Met Asp Pro Thr Asp Ala Lys Tyr His Met Gln Arg Cys Ile Asp Ser<br>325                      330                      335 | 1064 |
| GGC CTC TGG GTC CCC AAC TCT AAG GCC AGC GAG GCC AAG GAG GGA GAG<br>Gly Leu Trp Val Pro Asn Ser Lys Ala Ser Glu Ala Lys Glu Gly Glu<br>340                      345                      350                      355 | 1112 |

-continued

```
GAG GCA GGT CCT GGG GAC CCA TTA CTG GAA GCT GTT CCC AAG ACG GGC    1160
Glu Ala Gly Pro Gly Asp Pro Leu Leu Glu Ala Val Pro Lys Thr Gly
                360                 365                 370

GAT GAG AAG GAT GTC AGT GTG TGACCTGCCC CAGCTACCAC CGCCACCTGC       1211
Asp Glu Lys Asp Val Ser Val
                375

TTCCAGGCCC CTATGTGCCC CTTTTCAGAA AACAGATAGA TGCCATCTCG CCCGCTCCTG  1271

ACTTCCTCTA CTTGCGCTGC TCGGCCCAGC CTGGGGGCCC GCCCAGCCCT CCCTGGCCTC  1331

TCCACTGTCT CCACTCTCCA GCGCCCATTC AAGTCTCTGC TTTGAGTCAA GGGGCTTCAC  1391

TGCCTGCAGC CCCCCATCAG CATTATGCCA AAGGCCCGGG GGTCCGGGGA AGGGCAGAGG  1451

TCACCAGGCT GGTCTACCAG GTAGTTGGGG AGGGTCCCCA GCCAAGGGGC CGGCTCTCGT  1511

CACTGGGCTC TGTTTTCACT GTTCGTCTGC TGTCTGTGTC TTCTATTTGG CAAACAGCAA  1571

TGATCTTCCA ATAAAAGATT TCAGATGCTA AA                                1603
```

(2) INFORMATION FOR SEQ ID NO:7:

(i) SEQUENCE CHARACTERISTICS:
        (A) LENGTH: 378 amino acids
        (B) TYPE: amino acid
        (D) TOPOLOGY: linear (ii) MOLECULE TYPE: protein (xi) SEQUENCE DESCRIPTION: SEQ ID NO:7:

```
Met Val Asp Tyr Ser Val Trp Asp His Ile Glu Val Ser Asp Asp Glu
  1               5                  10                  15

Asp Glu Thr His Pro Asn Ile Asp Thr Ala Ser Leu Phe Arg Trp Arg
                 20                  25                  30

His Gln Ala Arg Val Glu Arg Met Glu Gln Phe Gln Lys Glu Lys Glu
             35                  40                  45

Glu Leu Asp Arg Gly Cys Arg Glu Cys Lys Arg Lys Val Ala Glu Cys
         50                  55                  60

Gln Arg Lys Leu Lys Glu Leu Glu Val Ala Glu Gly Gly Lys Ala Glu
 65                  70                  75                  80

Leu Glu Arg Leu Gln Ala Glu Ala Gln Gln Leu Arg Lys Glu Glu Arg
                 85                  90                  95

Ser Trp Glu Gln Lys Leu Glu Glu Met Arg Lys Lys Glu Lys Ser Met
            100                 105                 110

Pro Trp Asn Val Asp Thr Leu Ser Lys Asp Gly Phe Ser Lys Ser Met
        115                 120                 125

Val Asn Thr Lys Pro Glu Lys Thr Glu Glu Asp Ser Glu Glu Val Arg
    130                 135                 140

Glu Gln Lys His Lys Thr Phe Val Glu Lys Tyr Glu Lys Gln Ile Lys
145                 150                 155                 160

His Phe Gly Met Leu Arg Arg Trp Asp Asp Ser Gln Lys Tyr Leu Ser
                165                 170                 175

Asp Asn Val Leu Leu Val Cys Glu Glu Thr Ala Asn Tyr Leu Val Ile
            180                 185                 190

Trp Cys Ile Asp Leu Glu Val Glu Glu Lys Cys Ala Leu Met Glu Gln
        195                 200                 205

Glu Ala His Gln Thr Ile Val Met Gln Phe Ile Leu Glu Leu Ala Lys
    210                 215                 220

Ser Leu Lys Val Asp Pro Arg Ala Cys Phe Arg Gln Phe Phe Thr Lys
225                 230                 235                 240
```

```
Ile Lys Thr Ala Asp Arg Gln Tyr Met Glu Gly Phe Asn Asp Glu Leu
            245                 250                 255

Glu Ala Phe Lys Glu Arg Val Arg Gly Arg Ala Lys Leu Arg Ile Glu
            260                 265                 270

Lys Ala Met Lys Glu Tyr Glu Glu Glu Arg Lys Lys Arg Leu Gly
            275                 280                 285

Pro Gly Gly Leu Asp Pro Val Glu Val Tyr Glu Ser Leu Pro Glu Glu
    290                 295                 300

Leu Gln Lys Cys Phe Asp Val Lys Asp Val Gln Met Leu Gln Asp Ala
305             310                 315                 320

Ile Ser Lys Met Asp Pro Thr Asp Ala Lys Tyr His Met Gln Arg Cys
                325                 330                 335

Ile Asp Ser Gly Leu Trp Val Pro Asn Ser Lys Ala Ser Glu Ala Lys
            340                 345                 350

Glu Gly Glu Glu Ala Gly Pro Gly Asp Pro Leu Leu Glu Ala Val Pro
            355                 360                 365

Lys Thr Gly Asp Glu Lys Asp Val Ser Val
    370                 375
```

(2) INFORMATION FOR SEQ ID NO:8:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:8:

```
Glu Leu Gln Lys Cys Phe Asp Ala Lys Asp Val Gln Met Leu Gln
1               5                   10                  15
```

NUCLEIC ACID ENCODING VERTEBRATE CDC37

BACKGROUND OF THE INVENTION

The cell cycle is controlled by extracellular signals such as growth factors and growth inhibitors and, internally, by a series of kinases known as the cyclin-dependent kinases or cdk's. Cell cycle progression is largely dependent on the orderly activity of these cdk's. The first cyclin-dependent kinase identified was the cdc28 gene of the yeast *Saccharomyces cerevisiae*. Conditional mutants of cdc28 lead to G1 arrest. In the same genetic screen that identified cdc28, another gene which gave the same phenotype was discovered and termed cdc37. Although much has been learned about cdc28 and cyclin-dependent kinases in the last ten years, relatively little is known about cdc37. In yeast, the phenotype of cdc37 results from a failure to activate the cdc28 kinase in those cells. This failure appears to be due to an inefficient association of cdc28 with cyclins in the yeast *Saccharomyces cerevisiae*. This observation has led to the hypothesis that cdc37 might function as an assembly factor for the cdc28 cyclin complex.

Aberrant activity associated with molecules involved in cell cycle control is responsible, in some instances, for oncogenic transformation. Additional information relating to the interaction of cdc37 with other important cellular signalling molecules may provide the basis for targeted therapeutic intervention.

SUMMARY OF THE INVENTION

The subject invention relates, in one aspect, to a substantially pure nucleic acid sequence encoding vertebrate cdc37. The protein encoded by this nucleic acid is characterized by the ability to bind specifically to mammalian proteins selected from the group consisting of cyclin D, cdk4 and hsp90. In addition, the protein is further characterized by the ability to bind glycosaminoglycan. In preferred embodiments, the substantially pure nucleic acid sequence encoding cdc37 is characterized by the ability to hybridize specifically with the DNA represented in SEQ ID NOS: 1, 4 and 6 under stringent hybridization conditions.

The invention also relates to DNA expression constructs containing a substantially pure nucleic acid sequence encoding vertebrate cdc37 of the type described above. In addition, the invention relates to eukaryotic and prokaryotic cells which contain such an expression construct. Cells containing such expression constructs are useful, for example, for the production of cdc37 by recombinant DNA techniques. Cdc37, produced in this manner, can be used as immunogen for the production of antibodies. Thus, in related aspects, the invention encompasses monoclonal and polyclonal antibodies produced by recombinant DNA techniques.

Organic molecules (including peptides and other small molecules) which bind to components of the hsp90::cdc37::cdk4 complex also fall within the scope of the present invention. Organic molecules which interfere with the interactions between cdc37 and other important signalling molecules are also included in the subject invention. As discussed more fully below, such molecules find therapeutic application in connection with the treatment of malignancies.

DETAILED DESCRIPTION OF THE INVENTION

In one aspect, the present invention relates to human therapy and diagnostics. Recent advances make clear that the hallmark of the new generation of cancer therapeutics will be their exquisite specificity, as opposed to the relatively non-specific current therapies (e.g., methotrexate therapy) which target all growing cells rather than just tumor cells. Biopsies of cancerous cells will be taken and markers associated with specific cancer cell defects will be identified. For example, genetic mutation, amplification, overexpression, and underexpression of oncogenes and anti-oncogenes represent specific cancer cell defects. "Markers" for these defects, as that term is used herein, refers to any molecular embodiment of such defects which are detectable through the use of the arsenal of analytical methods currently available. Such methods include, for example, nucleic acid hybridization, PCR analysis, and antibody staining, to name a few. Therapies will then be developed which specifically target cells bearing the cancer-specific marker. This will result in less toxicity to the patient and will enable the clinician to increase drug dosage in appropriate circumstances.

Preliminary evidence gained through Northern blot analysis of 7 human cancer cell lines indicates a substantial increase in cdc37 expression, relative to non-malignant cells. This data is consistent with published reports of up regulation of cdc37 in v-src transformed cells (Ozaki et al., (1995) DNA Cell Biol. 14, 1017). Cdc37 is, therefore, a marker associated with a particular cancer cell defect.

Thus, in one aspect, certain compositions of the present invention are useful for the screening of biopsy tissue for the purposes of identifying whether a particular cancer cell is characterized by the overexpression of cdc37. Polyclonal and monoclonal antibodies specific for cdc37 can be used in conventional Western blot or in situ studies to determine whether the cells are overexpressing cdc37, relative to otherwise identical cells which are non-malignant. Based on the disclosure of the present invention, such antibodies can be produced through the application of routine experimentation. Nucleic acid hybridization using probes designed to be complementary to the cdc37 gene, or PCR analysis using primers complementary to defined regions of the gene can be used to identify amplification or overexpression of cdc37 at the genetic level. One of skill in the art can design primer or probe sequences by routine analysis of the sequence information provided below.

As indicated above, once the preliminary diagnostic work has been carried out, appropriate therapeutic strategies are designed. These strategies are designed to alter specific molecular interactions which are associated with the cancer cell defect. Focusing specifically on the role of cdc37 in human oncogenic transformation, it is known that a number of well-characterized molecules play a central role in such cell growth and transformation. These include, for example, cdk4 (cyclin-dependent kinase 4), D-type cyclins (e.g., cyclin D1), hsp90, and the retinoblastoma susceptibility protein (Rb). Cdk4 is a necessary regulatory molecule involved in the passage through sequential cell cycle transitions. As the name implies (cyclin-dependent kinase), cdk4 must associate with a cyclin D in order to become active as a kinase. The only known substrate for the cdk4 kinase is the tumor suppressor gene product, Rb. Rb has been shown to be deleted in a number of human tumors. The phosphorylation of Rb by cdk4 contributes to the inactivation of Rb which is required for cell cycle progression. Therefore, an important therapeutic goal in cancer therapy is to restore Rb function and/or decrease cdk4 activity to slow, or stop, malignant cell growth.

As reported in the Exemplification section which follows, cdc37 binds specifically with the mammalian G1 cyclin-dependent kinase cdk4, and with the heatshock protein hsp90. The binding data indicate that cdc37 forms complexes individually or in combinations with the cdc37 interacting proteins. The complex of cdc37 and hsp90 appears to stabilize the cdk4 protein and enhance its activity. Thus, therapeutic agents which would bind cdc37, thereby interfering with its binding to proteins such as cdk4 and hsp90, would be expected to lead to the destabilization of cdk4. This would, in turn, result in decreased growth of tumor cells, and possibly, their elimination. Similarly, therapeutic agents which would bind specifically to hsp90 or cdk4, thereby inhibiting complex formation, would be expected to exhibit similar effects.

The preceding sentence notwithstanding, cdc37 is likely a better target than, for example, hsp90 because the activities of cdc37 in a cell are limited relative to the activities of hsp90. If, for example, a compound were identified which could bind directly to hsp90, thereby inhibiting its activity, it is likely that such a molecule would interfere with other important molecular interactions which are not associated with the cancer phenotype. Therefore, compounds which bind directly to cdc37 are much less likely to interfere with the growth and development of non-malignant cells.

Thus, in one aspect, the present invention relates to organic molecules which bind a member of the hsp90::cdc37::cdk4 complex thereby inhibiting formation of the complex. In preferred embodiments, the compound binds specifically to cdc37 thereby inhibiting complex formation between cdc37, hsp90 and cdk4. In light of the fact that the binding data discussed above indicates that all three proteins can be found in a single complex, it seems clear that hsp90 and cdk4 interact with distinct sites on the cdc37 molecule. Hsp90 has been previously shown to be a chaperon protein, and inhibiting hsp90 function has been shown to lead to the destabilization of cdk4 and c-raf in cells. Thus, agents which inhibit development of cdc37/hsp90 complex would likely prevent cdk4 and c-raf from being stabilized by cdc37. Agents which prevent cdc37 from interacting directly with either cdk4, or c-raf, would also be expected to lead to the metabolic destabilization of these target proteins.

Organic molecules of the type described can be identified through screening of organic compounds for inhibitors of the interactions between cdc37, cdk4, hsp90 and c-raf from either existing libraries of such structures or libraries which are created, for example, by methods of combinatorial chemistry or genetics.

In addition to hsp90, another heat-shock protein, namely hsp60, was found to accumulate and form a complex with cdk4, cyclin D and hsp90 in the in vitro complex formation assays. Preliminary evidence also indicates that cdc37 is an important regulator of cdk4 activity not only by binding directly to individual components of the active complex (cdk4, cyclin Ds, heat-shock proteins and Rb), but also by mediating active communication ("cross-talk") among various cdks (cyclin-dependent kinases) and cell-cycle specific tyrosine kinases (i.e. Wee-1) and phosphatases (i.e., cdc25). Finally, the experiments demonstrate that vertebrate cdc37 interacts directly with the mammalian Rb protein and regulates positively its phosphorylation state. This is possibly mediated by an, as yet unidentified Rb kinase (most probably cdk1/2 related), which is brought by the cdc37 direct interaction. Notably, cdc37 binds to the carboxy-terminal third of the Rb protein, an area reported to be crucial for the regulation of Rb.

Deletion analysis of the vertebrate cdc37 genes has shown that in addition to the Rb binding motif, other amino acid motifs (residing both at the amino terminus of the cdc37 common domain and at the unique carboxy-ends of the cdc37 molecules isolated) determine Rb binding specificity.

Experiments performed using both stably and transiently expressed cdc37 in mammalian cells, alone or in combination with other known signalling molecules, have further revealed that cdc37 proteins encoded by the cDNAs disclosed herein play important roles in both ras and ras-independent signalling pathways including those utilizing MAP (microtubule associated proteins) kinases. In order to gain insight into the mechanisms underlying the effects of cdc37 in growth factor and stress-related cell signalling, several known signalling proteins have been tested and identified as specifically interacting with cdc37. These include (in addition to the above-mentioned raf family of proteins and hsp90) the phosphatidyl-inosital 3-kinase (P13-K), the stress-activated protein kinase (SAPK), the MAPK kinase Mek-1, and the ERK-1. The latter was found to interact with hsp90 after stimulation by phorbol esters and, therefore, in the same complexes with cdc37/hsp90. Both coimmunoprecipitation assays, followed by antibody detection and coexpression studies have been used to detect the above associations.

Finally, since a 50 kd protein has also been reported to complex with the src family of proteins, the possibility that cdc37 was involved in this interaction was investigated. This seemed likely given the report in the yeast system that a cdc37 mutant strain was not permissive in v-src kinase signalling. Both in vivo (coexpression assays) and in vitro (by GST-cdc37 protein interaction assays using v-src stable cell line extracts) cdc37 was found to associate with a specific complex of proteins which included v-src, hsp90, hsp70 and v-src tyrosine phosphorylated proteins. Furthermore, in in vitro kinase assays it has been demonstrated that an active kinase, possibly v-src, is included in the above protein complex. Thus, directly, or through its heat-shock partner hsp90, cdc37 is able to bind multiple kinases (cdk4, raf, src kinases, SAPK, MAPK, Rb and Wee-1) and regulate their function. For this reason, cdc37 can be considered an essential molecule in cell cycle and growth-factor signalling events. Collectively, the proteins identified herein as binding specifically to cdc37 will be referred to as the cdc37 interacting proteins.

Organic molecules which will bind cdc37 or any of the cdc37 interacting proteins, thereby inhibiting or potentiating binding with cdc37 will influence the cell cycle and cell signalling events. Such molecules have direct therapeutic application, for example, in the treatment of malignancies.

In another therapeutic embodiment, drugs effective in decreasing cdc37 expression levels can be administered in appropriate circumstances. Cdc37 mutations in both yeast and fruit flies have been shown to lead to growth inhibition. The data for the mammalian cdc37 indicate that cdc37 is upregulated in tumor cells and during periods of rapid growth. Therefore, drugs which decrease levels of cdc37 in cells would be anticipated to lead to reduced cell proliferation or inhibition of tumor cell growth. A specific example of a drug which would inhibit cdc37 is the transcribed product of a reverse cdc37 gene construct (i.e., an antisense construct). Methods of construction and use of such antisense constructs are well known in the literature. Given the present disclosure, it is a matter of routine experimentation to design an effective antisense construct for use in human therapy to reduce cdc37 expression. Methods for the identification of other organic compounds useful for the inhibition of transcription of cdc37 will be apparent to those skilled in the art.

Subunits of cdc37 could also be used as dominant inhibitors of the wild-type cdc37 function. The fact that hsp90 and cdk4 can be found in the same complexes with cdk4 and cdc37 suggests that there are independent binding domains on cdc37 for hsp90 and cdk4. Consider, for example, expression of the domain of cdc37 which interacts with cdk4, in the absence of the domain which interacts with hsp90. Such expression should prevent the wild type hsp90::cdc37 complex from interacting with cdk4. Such protein subdomains could be delivered therapeutically directly as purified peptides or synthetic peptides. Alternatively, DNA encoding such domains could be introduced into appropriate cells using gene therapy vectors.

An additional utility associated with the cdc37 gene product is based on its glycosaminoglycan (GAG) binding properties. As discussed more fully below, vertebrate cdc37 is a novel GAG binding protein. GAGs are a family of structurally heterogeneous polysaccharides found on proteoglycans. Assays employing GAG binding proteins have been demonstrated to be useful in assessing relationships between GAG structure and binding (see, e.g., Lee and Lander, (1991) Proc. Natl. Acad. Sci. USA 88, 2768).

A specific example which demonstrates the usefulness of a GAG binding protein is in the analysis of the heparin molecule. Heparin is a naturally occurring proteoglycan (a collection of GAG chains linked to a central protein core) with a molecular weight of about 1,000,000. Heparin is known to bind to and modulate the activity of a wide variety of proteins including antithrombin III. In addition, heparin binds C1, C3, C1-inhibitor, factor H and C4 binding protein of the complement system with a net effect of inhibiting complement activity. In addition, heparin is known to bind to and augment the activity of growth factors including acidic fibroblastic growth factor.

Currently, heparin is widely used as an anticoagulant. Commercial processing of heparin results in a mixture of polysaccharide chains of varying lengths and varied structure with an average molecular weight of 9,000–15,000 called GAG heparin. Species within this group are known to bind antithrombin III with high affinity, while others bind with low affinity. The use of GAG binding proteins as affinity reagents for affinity electrophoresis enabled the separation and characterization of the individual heparin GAG species which comprise this polydisperse mixture.

Through the use of such methods, it is possible to characterize high affinity binding species based, for example, on their molecular weight. Heparin preparations which are enriched for high affinity binding would offer advantages as an anticoagulant. This approach could also be employed to screen for GAG species which could inhibit complement activity by using one of the complement proteins which is known to bind heparin as the GAG binding protein in the first dimension separation.

The isolation of nucleic acids encoding cdc37, as described more fully below, facilitates the uses described above. In addition to the sequences specifically disclosed, the present invention also encompasses nucleic acids which hybridize to disclosed nucleic acid sequences under stringent hybridization conditions. Stringent hybridization conditions, as used herein, refer to hybridization in which the target DNA molecule is fixed to a solid support and a second DNA molecule to be tested for the ability to hybridize to the target DNA molecule is detectably labeled and suspended in a hybridization buffer consisting essentially of 50% formamide, 5×SSPE (1×SSPE is 0.15 mM NaCl, 1 mM Na-EDTA, 10 mM Na-phosphate (pH 7.0), 5×Denhardt's solution (0.1% polyvinylpyrrolidone, 0.1% Ficoll)). The hybridization buffer is contacted with the solid support at a temperature of about 45° C. for a period of several hours. The hybridization solution is then removed, and non-specifically bound nucleic acid is removed by repeated washing with 1×SSC at increasing temperatures (up to 65° C.).

EXAMPLES

Example 1

Materials and Methods

Materials

The $^3$H-hyaluronan, mAb IVd4, hyaluronan hexaccharides, and biotinylated hyaluronan were produced as described elsewhere (Underhill and Toole, (1979) J. Cell Biol. 82, 475–484; Banerjee and Toole, (1991) Dev. Biol. 146, 186–197; Pouyani et al., (1994) Bioconjugate Chem. 5, 370–372). Chondroitin sulfate and heparin were purchased from Sigma (St. Louis, Mo.). Restriction and modification enzymes and the kits used for 5' and 3' RACE experiments were purchased from Bethesda Research Laboratories (Gaithersburg, Md.). Kits for immunoscreening and generation of probes by random priming were from Stratagene (La Jolla, Calif.). The in vitro transcription and translation kit was from Promega (Madison, Wis.) and radionucleotides from NEN (Boston, Mass.) or ICN Radiochemicals (Irvine, Calif.). Nitrocellulose membranes used for plaque lifts and agarose blotting were from Millipore (Bedford, Mass.) and Schleicher and Schuell (Keene, N.H.), respectively. Taq polymerase and the reverse transcriptase-PCR kit were supplied by Perkin Elmer (Norwalk, Conn.). Ingredients for media preparation were from GIBCO (Gaithersburg, Md.). Vectastain ABC kits were from Vector Laboratories (Burlingame, Calif.). Autoradiography was done using Kodak XAR X-ray film. oligonucleotide primers were prepared in facilities at Tufts Medical School.

Expression Library Screening with mAb IVd4

A chick embryo cardiocyte library (cDNA made from polyA+ mRNA ligated into the EcoRI and XhoI sites of UNIZAP XR) was used as a source of cDNA clones. A total of 2×10$^5$ plaques were screened with mAb IVd4. Bound antibody was detected with goat anti-mouse alkaline phosphatase-conjugated antibody and Nitro Blue Tetrazolium according to manufacturer's instructions (Stratagene). Phage clones were plaque purified after two more rounds of screening; plasmid that was in vivo excised from the phage was then induced for beta-galactosidase fusion protein production in liquid culture. Using the XbaI and KpnI sites present in the polylinker of the pBluescript KS(+) vector, cDNA inserts were subcloned into M13 mp19 for deletion construction and sequencing.

Nucleic Acid Hybridizations

Nitrocellulose membranes were pre-hybridized for 2–4 h in a solution containing 50% deionized formamide, 5×SSC (0.75M NaCl, 0.075M Na citrate, pH 7.0), 50 mM Na phosphate (pH 6.5), 5×Denhardt's, 200 μg/ml sheared salmon sperm DNA, and 0.1% SDS prior to incubation with random-primed probes (Feinberg and Vogelstein, (1984) Anal. Biochem. 132, 6–13) at 42° overnight in fresh hybridization solution. The membranes were then washed twice for 30 min each at 56° in 0.1×SSC, 0.1% SDS, and exposed to X-ray film overnight with an intensifying screen at −80°.

Northern Blotting

Total RNA was isolated from chick embryo heart by the acid guanidinium thiocyanate-phenol-chloroform extraction method (Chomczynski and Sacchi, (1987) Anal. Biochem.

162, 156–159), fractionated in 1.2% denaturing agarose gels containing 2.2M formaldehyde, and blotted onto nitrocellulose (Sambrook et al., (1989) Molecular Cloning: A Laboratory Manual, 2nd Ed., Cold Spring Harbor Laboratory, Cold Spring Harbor, N.Y.). In order to detect the low abundance 0.9 kb transcript, it was necessary to hybridize blots containing 20–25 μg of RNA in the presence of 1% dextran sulfate with high specific activity, anti-sense probes. To prepare the probe used, single-stranded DNA (0.5 μg) from a M13 mp19 construct containing the entire pNG13 insert was annealed to M13 universal primer in 10 mM Tris-HCl, 10 mM $MgCl_2$, 75 mM DTT, pH 7.5, at 65° for 5 min. The anti-sense (non-coding) strand of the insert was homogeneously radiolabeled using DNA polymerase I (Klenow fragment) and 100 μCi [alpha-$^{32}$P] dCTP plus dATP, dGTP and dTTP (0.5 mM each) at 37° for 20 min. The reaction product was subsequently digested with EcoRI which cuts at the multiple cloning site of the vector. The resulting 0.8 kb single-stranded fragment was purified by electroelution on a 6% sequencing gel and used as a probe at $10^7$ cpm per ml of hybridization solution.

Rapid Amplification of cDNA Ends (RACE)

Poly $A^+$ RNA was obtained by oligo-dT chromatography from 15 day chick embryo heart total RNA. 3' and 5' RACE (Frohman et al., (1988) Proc. Natl. Acad. Sci. USA 85, 8998–9002) were performed using reagent kits and modified instructions supplied by the manufacturer (Bethesda Research Laboratories). For 3' RACE, cDNA synthesis was primed from 25 ng of cardiac mRNA with an oligo-dT-containing adapter primer, followed by extension with M-MLV reverse transcriptase. After digestion with RNase H and purification of the cDNAs, amplification was performed using a 3'-specific sense primer corresponding to nucleotide positions 685–716 of the pNG13 cDNA presented in SEQ ID NO: 1 and the universal adapter primer provided by the supplier. A second amplification was carried out using a nested primer (nt 750–773) and the universal adapter primer. For 5' RACE, first strand cDNA was synthesized from 10 ng mRNA by incubation with 2.5 pmoles of a 5' specific antisense primer (corresponding to nt 208–234 of pNG13) and M-MLV reverse transcriptase at 42° for 30 min. After removal of the initial primer and mRNA, the cDNA was tailed with dCTP and terminal transferase. Subsequent AmpliTaq (Perkin Elmer) amplification was done with nested antisense primers (nt 135–157 and nt 112–137) and a deoxyinosine-containing anchor primer (Bethesda Research Laboratories).

Denaturation, annealing and extension were performed for 30 sec at 94°, 30 sec at 60°, and 1 min at 72°, respectively, for 30 cycles. 3' and 5' RACE PCR products were visualized by ethidium bromide staining and, after subcloning in pCRII (Invitrogen, Irvine, Calif.), they were sequenced and compared to the 3' and 5' nt ends, respectively, of the pNG13 cDNA.

Western Blotting and Hyaluronan Binding Procedures

Expression of cDNA-encoded protein using the pBluescript vector was induced by growing the bacterial culture to an $OD_{600}$ of 0.5 and then adding isopropyl-thiogalactoside (IPTG) to a final concentration of 1 mM. The cultures were grown for an additional 1 h, pelleted by centrifugation, resuspended in 5 mM Tris-Cl (pH 8.0), 1 mM EDTA, 1 mM PMSF, 10% sucrose, and lysed by sonication. The lysates were mixed with an equal volume of SDS-PAGE sample buffer and electrophoresis was performed in 12% SDS-polyacrylamide gels. The gels were stained in Coomassie Blue or blotted to PVDF for reaction with antibody or with hyaluronan.

Western blots (Towbin et al., (1979) Proc. Nat. Acad. Sci. USA 76, 4350–4354) were reacted with mAb IVd4. Hyaluronan-binding was measured by two different methods. In the first method the blot was reacted with $^3$H-hyaluronan as described previously (Banerjee and Toole, (1991) Dev. Biol. 146, 186–197). In the second method, the blot was reacted with biotinylated hyaluronan. The biotinylated hyaluronan was made using hydrazido-hyaluronan according to instructions provided by Pierce (Rockford, Ill.) and also described in Pouyani et al. ((1994) Bioconjugate Chem. 5, 370–372). Specificity of interaction in these methods was confirmed by competition with hyaluronan, hyaluronan oligosaccharides and other GAGs.

in vitro Transcription and Translation pNG13 in pBluescript SK vector was used as template with T7 RNA polymerase to synthesize RNA transcripts in vitro. The RNA was translated in a rabbit reticulocyte lysate system (Promega, Madison Wis.) containing [$^{35}$S] methionine. in vitro translation products were separated by SDS-PAGE and visualized by fluorography.

Nucleotide Sequencing and Computer Analyses

Prospective hyaluronan-binding protein phage clones were in vivo excised to their pBluescript forms and their inserts were subcloned into M13 mp19. Overlapping 3' deletions for each of the two DNA strands were then generated with $T_4$ DNA polymerase by the method of Dale et al. ((1985) Plasmid 13, 31–40) and sequenced with Sequenase (USB Biochemicals, Cleveland Ohio). When necessary, PCR sequencing was performed and formamide denaturing PAGE was used.

Nucleic acid and protein sequence data were analyzed with DNASIS (Hitachi Co., Tokyo) and University of Wisconsin Genetics Computer Group software. Sequence comparisons against the Genbank-EMBL and NBRF databases were performed using the FASTA program (Pearson and Lipman, (1988) Proc. Nat. Acad. Sci. USA 85, 2444–2448). Multiple alignments and statistical analysis of sequence similarity between two protein sequences was obtained using the Pretty and the Bestfit programs, respectively, of the University of Wisconsin Genetics Computer Group (version 7.3).

RESULTS

Expression Cloning of cDNA for IVd4 Antigen

Since immunohistochemical staining of chick embryo heart with mAb IVd4 showed strong immunoreactivity in both the myocardium and the endocardium, a chick embryo cardiac muscle cell library was screened for immunoreactivity with mAb IVd4. Of several clones that were immunopositive over successive rounds of screening, clone lambda-NG13 displayed consistently strong immunoreactivity with IVd4. The phage clone was isolated and, after in vivo conversion to its pBluescript plasmid form, it was used for sequencing, mapping and preparation of beta-galactosidase fusion protein.

Aliquots of total bacterial extract containing the induced fusion protein were separated by SDS-PAGE and transblotted. The transblots were then overlayed with mAb IVd4, or with $^3$H-hyaluronan in the presence and absence of hyaluronan oligosaccharides (Banerjee and Toole, (1991) Dev. Biol. 146, 186–197) to verify that the protein encoded by the selected cDNA was indeed a IVd4-reactive, hyaluronan-binding protein. The Western blot with IVd4 revealed three bands of molecular weights 36, 29 and 22 kDa. The largest of these polypeptides corresponds in size to that expected for the full length beta-galactosidase fusion protein. The two smaller polypeptides presumably represent degradation products of the full-length protein or internally initiated polypeptides. The $^3$H-hyaluronan overlay showed a major peak of $^3$H-hyaluronan binding that corresponded exactly in electrophoretic migration to the full length IVd4-reactive fusion polypeptide, and a smaller peak of binding that spread over the region of the two smaller size polypeptides. Since hyaluronan hexasaccharides competitively inhibit binding of $^3$H-hyaluronan to IVd4-reactive proteins (Banerjee and Toole, (1991) Dev. Biol. 146, 186–197), they were included in the reaction mixture as a control for specificity in the binding assay. The binding of $^3$H-hyaluronan to the fusion proteins was eliminated in the presence of these oligosaccharides.

To confirm the hyaluronan-binding data by a direct visual method, biotinylated hyaluronan was also used to detect binding to discrete protein bands on the transblots (Yang et al., (1994) EMBO J. 13, 286–296). Once more, hyaluronan binding was detected mainly to a recombinant protein of ~36 kDa, and this binding was inhibited by hyaluronan hexasaccharides. In this set of experiments, the ability of other GAGs to compete for hyaluronan binding was also tested and it was found that chondroitin sulfate and heparin inhibited hyaluronan binding to the protein encoded by pNG13. Thus, this protein exhibits general GAG-binding properties.

Molecular Characterization of pNG13

The ~900 bp insert of clone pNG13, devoid of its poly(A) tail, was radiolabeled and hybridized with a Northern blot containing chick embryo heart RNA. Under stringent hybridization conditions, the pNG13 insert recognized two mRNAs: a prominent band of ~1700 nt and a faint band of ~900 nt. Although the signal obtained at ~900 nt was weak, we believe that this rare mRNA corresponds to the pNG13 cDNA, and that pNG13 is virtually full-length, for the following reasons. First, the size of the pNG13 cDNA and its encoded polypeptide are consistent with a 900 nt mRNA. Second, 5' and 3' RACE failed to extend the pNG13 cDNA sequence except for two additional residues at the 5' end. Third and most importantly, the cloning and characterization of a second cDNA, corresponding in size to the prominent 1700 nt mRNA but having an entirely different 3' sequence, indicate that this larger mRNA and the relatively minor 900 nt mRNA may arise from the same gene by alternative splicing; details of this cDNA (pNG17) which encodes a protein lacking the mAb IVd4 epitope are given below.

Nested M13 deletions were generated to accurately determine the full sequence of pNG13 (SEQ ID NO: 1). The 894 bp, polyadenylated cDNA contains a single uninterrupted open reading frame of 738 bp, beginning at the first ATG codon at nucleotide position 64. This ATG codon is in frame with the beta-galactosidase fusion protein and is surrounded by nucleotides conforming to the Kozak consensus for eukaryotic translation start signals (Kozak, (1987) Nucl. Acids Res. 15, 8125–8149; Kozak, (1991) J. Cell Biol. 115, 887–903). The deduced amino acid sequence following this potential initiation codon does not have the properties of a signal peptide that would be expected for a cell surface or extracellular GAG-binding protein, implying that it is probably intracellular. Although mAb IVd4 clearly detects extracellular or cell surface antigen(s) and elicits effects that would depend on such localization, it also recognizes intracellular antigen(s) (Banerjee and Toole, (1992) J. Cell Biol. 119, 643–652). Thus the putative intracellular localization of the IVd4-reactive protein encoded by pNG13 is consistent with past findings but confirms that the IVd4 epitope is present on more than one protein.

The first in-frame termination codon within pNG13 is located at position 802 and overlaps with the polyadenylation signal found 15 nucleotides before the poly(A) tail. This cDNA therefore has an unusually short 3' untranslated region composed of only 18 nucleotides between the stop codon and the poly(A) tail. Short 3' untranslated regions have been noted previously and can include an overlap between the termination codon and the polyadenylation signal as found here (Kawajiri et al., (1983) J. Biochem. 94, 1465–1473; Furukawa et al., (1990) J. Biochem. 108, 297–302; Lustigman et al., (1992) J. Biol. Chem. 267, 17339–17346). Also, 3' sequence validity has been confirmed by further nucleic acid library screening, in which an additional cDNA has been isolated whose sequence has an identical 3' untranslated region to pNG13. Furthermore, reverse transcriptase-PCR using primers spanning the C-terminal coding and 3' untranslated regions gives products of the expected size.

Assuming that the open reading frame does initiate at the codon discussed above, it would encode a 246 amino acid polypeptide, with a calculated molecular mass of 29.3 kDa. When expressed in a eukaryotic in vitro translation system, a major polypeptide of molecular weight, ~31 kDa, was produced. The largest of the bacterial fusion proteins obtained by expression in pBluescript was ~36 kDa, which also corresponds well to an encoded product of 29.3 kDa after subtraction of the beta-galactosidase fragment of the fusion protein and the following in-frame sequence corresponding to the 5' untranslated region of the cDNA (a total of 7.4 kDa). The expected sizes were also obtained in other prokaryotic expression systems, including pGEX which has been used to prepare purified fusion protein. Therefore, the deduced open reading frame is compatible with the size of the fusion proteins produced in bacterial systems and with the protein produced by in vitro translation of pNG13. This sequence was also found to conform to various established criteria (test code, codon preference) for avian-specific cDNAs.

Isolation of a splicing isoform related to pNG13

To search for additional clones related to pNG13, we used the entire pNG13 cDNA as a probe in library hybridization experiments. This approach led to identification of 4 additional positive cDNA clones. These cDNA clones, which were all polyadenylated, were characterized by restriction mapping, Southern hybridization, and nucleotide sequencing. One of the clones was found to be a 5' truncated version of the pNG13 cDNA whereas the other three clones possess a 3' proximal region that is entirely different from pNG13. Further analysis revealed that these three cDNAs have overlapping, exactly matched sequences with each other and they are all identical to pNG13 up to nucleotide 588. Beyond residue 588, the three clones differ from pNG13 in that they have a unique 3' sequence exhibiting no homology with the corresponding region of pNG13.

The 5' terminal nucleotide residues of the above cDNAs were found by sequencing to correspond to nt 214 and 442 of pNG13, the two smaller cDNAs being identical. The largest of these cDNAs, pNG17, lacks 213 nt corresponding to the 5' end of pNG13. As stated above, nt residues 214–588 of pNG13 are identical to the 5' end of pNG17, but thereafter the sequences are entirely different. The open reading frame of pNG17 continues for 129 nt and is then followed by a relatively long, T-rich, 3'-untranslated region of 841 nt. The unique sequence of the pNG17 cDNA is presented in SEQ ID NO: 3.

To test whether this polyadenylated cDNA is truncated at the 5' end, 5' RACE was employed, using an antisense primer corresponding to nt 273 to 295 of pNG13 and overlapping by 82 bp at the 5' end of the 5' truncated pNG17 clone. This primer directed the synthesis of a PCR product of 295 bp whose sequence matches exactly with the 5' end of pNG13. Assuming, therefore, that the full-length pNG17 cDNA also originates at the 5' end of pNG13, the full size of this cDNA would be 1558 nt, which agrees well with the size of the major 1700 nt polyadenylated mRNA detected by hybridization with pNG13. Indeed, a fragment derived from the unique 3' untranslated region of pNG17 was found to detect only the 1700 nt mRNA isoform after rehybridization of the blot discussed above. These results indicate the existence of two related mRNAs that possess identical 5' moieties but differ at their 3' ends, presumably due to alternative splicing.

Whereas mAb IVd4 recognizes the pNG13-encoded protein, the antibody failed to recognize the fusion protein produced by the pNG17-pBluescript construct after SDS-PAGE and Western blotting. To further localize the IVd4 epitope in the pNG13-encoded protein, Western blotting of IPTG-induced bacterial extracts containing overlapping, carboxy-terminally truncated mutants of the pNG13 protein was employed. These mutants were produced by placement of the pNG13 cDNA insert adjacent to the lacZ promoter and in frame with the m19M13 vector beta-galactosidase gene, followed by exonuclease digestion to create overlapping 3' deletion M13 subclones. The IVd4 epitope was found to lie within a 15 amino acid region (ELQKCFDAKDVQMLQ) (SEQ ID NO: 8) near the carboxy terminus of the pNG13-encoded protein. The position of this epitope lies in the region unique to pNG13, thus explaining its absence in pNG17 and the failure to detect this cDNA in the initial immunoscreening.

The pNG13 cDNA Encodes an Avian Homologue of cdc37

Computer searches of the available protein sequences revealed strong identity within the polypeptide sequences encoded by pNG13, pNG17 and Drosophila cdc37 (Cutforth and Rubin, (1994) Cell 77, 1027–1036), as well as, albeit to a lesser extent, cdc37 from yeast (Ferguson et al., (1986) Nucl. Acids Res. 14, 6681–6697). The aligned polypeptides were compared in Grammatikakis et al. ((1995) J. Biol. Chem. 270, 16198–16205). Homology with Drosophila and yeast cdc37 extends over the major part (amino acids 3–242) of the 246 amino acid chick pNG13 sequence, after which the polypeptides are dissimilar from each other. Notably, this is the area of homology between the Drosophila and yeast polypeptides, outside of which they are also dissimilar. Since pNG17 is identical with pNG13 only up to amino acid residue 175, this is also the extent of homology between the pNG17-encoded protein and cdc37. No significant homologies were found between the unique, carboxy terminal region of pNG17 or its 3' untranslated region and cdc37 or other cDNAs in the data bank. Thus further comparisons are made only between the pNG13-encoded protein and cdc37.

Over the area of homology between pNG13 and cdc37, the chick polypeptide (M1 to P242) is 57% identical to a corresponding, 245-amino acid, central portion of the 389 amino acid Drosophila sequence (E96 to P340), and 22% identical to a 295-amino acid region within the 440 amino acid yeast sequence (L103 to I397). Considering conserved amino acid substitutions, the degrees of similarity rise to 62% between chick and Drosophila and 30% between chick and yeast. In comparison, the identity between Drosophila and yeast sequences is also 22%, and the degree of similarity is 30%. It appears, therefore, that the yeast sequence has diverged at similar rates from each of the two metazoan counterparts. The yeast polypeptide is identical over 15% of its amino acid residues with the consensus between chick and Drosophila sequences. However, 29% of the residues within the yeast sequence are identical to one or the other of the chick or Drosophila sequences at any given amino acid position in the aligned polypeptides. This value increases to 40% by including conservative amino acid substitutions.

Despite the great phylogenetic distance between insect and vertebrate lineages, the cdc37 sequences of Drosophila and chick show a high degree of conservation at the amino acid level over the entire length of the shorter avian polypeptide. Three of the cysteines within the chick sequence (residues 131, 206, and 234) are also present in the same positions in the Drosophila sequence while no cysteines appear in the yeast counterpart. Another structural similarity between the chick and Drosophila proteins is that both could potentially form extensive alpha-helical domains throughout their length. An alpha-helical structure has also been predicted for yeast cdc37 (Ferguson et al., (1986) Nucl. Acids Res. 14, 6681–6697). In addition, Cutforth and Rubin ((1994) Cell 77, 1027–1036) have reported that the Drosophila cdc37 homologue was able to complement the corresponding cdc37 mutation in yeast cells.

From the above observations it appears that the chick homologue of the cell cycle protein, cdc37, has been isolated. However, the fact that the chick polypeptide is significantly shorter than the Drosophila or yeast forms would suggest that the cDNA isolated here may represent a different splicing variant than those described in Drosophila and yeast, or that the cloned chick cDNA is not full-length. The latter seems unlikely because of the reasons discussed above, i.e., size correspondence with the 900 nt mRNA, lack of extension of the sequence by 5' and 3' RACE, identification of multiple phage isolates with the same sequence as that presented for pNG13 in SEQ ID NO: 1, and the documentation that this cDNA contains all the appropriate elements for expression of a eukaryotic protein. In addition, hypothetical translation of the 63 nucleotides preceding the initiator codon indicated in SEQ ID NO: 1 did not reveal any amino acid sequence homology with the amino terminus of either the Drosophila or yeast polypeptides, which are themselves dissimilar to each other in this region. However, the possibility that the chick mRNA could also initiate further upstream can still not be conclusively ruled out, especially since no in-frame termination codon was detected in the 63 nt putative 5' untranslated region.

With respect to the possibility of multiple isoforms, first Southern blotting of genomic DNA revealed that there is most likely a single gene expressing cdc37. Second, another chick isoform has been characterized, pNG17, corresponding to the abundant 1.7 kb mRNA. This isoform shares exactly the same 5' coding region with pNG13 but its 3' coding and untranslated regions are entirely different from pNG13. Interestingly, the unique 3' coding and untranslated regions of this isoform also have no significant similarity to any part of the Drosophila or yeast cdc37 cDNAs. pNG13 and pNG17 cDNAs apparently correspond to mRNAs produced by alternative splicing in the avian cells. Thus it can be concluded that the protein encoded by pNG13 is homologous with the central coding domain of Drosophila and yeast cdc37, but that pNG13 encodes a shorter protein than the Drosophila and yeast counterparts. It is not yet fully clear whether chick cells express a homologous protein similar in size to these other species in addition to the proteins encoded by pNG13 and pNG17, whether pNG13 is a truncated cDNA despite the evidence to the contrary, or whether the chick produces the pNG13 and pNG17-encoded proteins rather than the isoform found in Drosophila and yeast. However, since the complete genomic sequence of Drosophila CDC37 has been reported (Cutforth and Rubin, (1994) Cell 77, 1027–1036), the exonic boundaries of the Drosophila gene have been compared with the sequence of pNG13. In doing so, it was observed that the 5' end of the pNG13 cDNA corresponds exactly with the 5' border of exon 3 of the Drosophila gene. Thus, transcription of chick cdc37 mRNA may originate at this position, giving rise to a mRNA that is two exons shorter than the Drosophila mRNA. Although a detailed analysis of the chick CDC37 structural gene would be necessary to confirm this unequivocally, the existence of a second chick cdc37 isoform, pNG17, whose 5' end apparently coincides with that of pNG13 when extended to its full length, supports this hypothesis. The total length of the extended pNG17 cDNA (1558 bp) agrees closely with the size of the predominant ~1700 nt polyadenylated mRNA species detected by Northern analysis. In contrast, if transcription of the chick CDC37 gene begins at the same position as in Drosophila, a 2000–2100 nt polyadenylated mRNA would then be predicted in the chick tissues, well above the size of the 1700 nt mRNA detected. It is also noteworthy that the 5' ends of the Drosophila and yeast cdc37 cDNAs are dissimilar from each other both in their sequences and in their lengths (Ferguson et al., (1986) Nucl. Acids Res. 14, 6681–6697; Cutforth and Rubin, (1994) Cell 77, 1027–1036).

The above conclusion that pNG13 encodes a chick cdc37 isoform, together with the lack of a definitive signal sequence at the beginning of the open reading frame, implies that the pNG13-encoded protein is intracellular. As noted above, intracellular immunoreactivity with mAb IVd4 has been noted previously (Banerjee and Toole, (1992) J. Cell Biol. 119, 643–652) but recognition of this intracellular protein is presumably not responsible for the inhibitory action of mAb IVd4 on cell behavior in culture (Banerjee and Toole, (1992) J. Cell Biol. 119, 643–652; Yu et al., (1992) Dev. Dynamics 193, 145–151; Toole et al., (1993) In: Limb Development and Regeneration, J. F. Fallon, P. F. Goetinck, R. O. Kelley, and D. L. Stocum, eds, Wiley-Liss, New York, pp.437–444). As also noted above, mAb IVd4 recognizes several proteins, the major species having molecular weights between 35 and 90 kDa. The results presented here are consistent with the smallest of these proteins being cdc37.

Comparison of the Putative Chick cdc37 with Other Known GAG-binding Proteins

The binding regions of many hyaluronan-binding proteins lie within characteristic loops that are often tandemly repeated (Goetinck et al., (1987) J. Cell Biol. 105, 2403–2408; Zimmermann and Ruoslahti, (1989) EMBO J. 8, 2975–2981; Rauch et al., (1992) J. Biol. Chem. 267, 19536–19547; Jaworski et al., (1994) J. Cell Biol. 125, 495–509). This type of structure was not detected within chick cdc37. However, analysis did reveal the hyaluronan-binding motif, [-B($X_7$)B-], where B is arginine or lysine, X is any non-acidic amino acid, and at least one additional basic amino acid lies within or adjacent to the motif (Yang et al., (1994) EMBO J. 13, 286–296). In chick cdc37, this motif occurs between amino acid residues R160 to R168. Yang et al. ((1994) EMBO J. 13, 286–296) also found that significant hyaluronan-binding was obtained to polypeptides where slight changes were introduced into the motif, [-B-($X_7$)B-], provided basic residues remained within or flanking the motif. Thus the sequence between residues K55 and R65 which has 4 basic residues within a [-B($X_8$)B-] motif could most likely also mediate hyaluronan binding. These two motifs are present in both the pNG13- and pNG17-encoded proteins. Considerable evidence has been obtained that motifs of this nature are necessary for hyaluronan binding in several GAG-binding proteins, whether or not they contain the above-mentioned tandemly repeated loops (Yang et al., (1994) EMBO J. 13, 286–296). Heparin-binding proteins also employ a variety of binding motifs that are highly enriched in basic amino acids and non-random in sequence (Cardin and Weintraub, (1989) Arteriosclerosis 9, 21–32; Sobel et al., J. Biol. Chem. 267, 8857–8862; Pratt et al., (1992) J. Biol. Chem. 267, 8795–8801). In fact, the two [-B($X_7$)B-] motifs present in the RHAMM (Receptor for Hyaluronan Mediated Motility) protein, where they were first characterized, bind both hyaluronan and heparin but not chondroitin sulfate or dermatan sulfate (Yang et al., (1994) J. Cell. Biochem. 56, 455–468.

A significant point of interest is the variable specificity of the known GAG-binding proteins despite the presence of similar binding motifs. Link protein and the hyaluronan-binding regions of proteoglycans are specific for hyaluronan (Hascall, (1977) J. Supramol. Struct. 7, 101–120; Yamagata et al., (1986) J. Biol. Chem. 261, 13526–13535; Goetinck et al., (1987) J. Cell Biol. 105, 2403–2408; Perides et al., (1992) J. Biol. Chem. 267, 23883–23887; LeBaron et al., (1992) J. Biol. Chem. 267, 10003–10010). CD44 recognizes only hyaluronan or chondroitin when present within the cell membrane but also recognizes chondroitin sulfate when in solution or in artificial membranes (Underhill et al., (1983) J. Biol. Chem. 258, 8086–8091; Chi-Rosso and Toole, (1987) J. Cell. Biochem. 33, 173–183). RHAMM recognizes hyaluronan and heparin only (Yang et al., (1994) J. Cell. Biochem. 56, 455–468), and the protein described here recognizes hyaluronan, chondroitin sulfate and heparin. Despite this variability, the hyaluronan-binding motifs in RHAMM, CD44 and link protein all conform to the [-B($X_7$)B-] sequence (Yang et al., (1994) EMBO J. 13, 286–296). It is not yet clear whether separate sequences within the proteins influence the specificity of binding of this motif, whether the motif itself varies in its specificity according to its own precise sequence, or whether factors such as conformation or interactions with other molecules confer the different specificities. The last possibility is supported by the influence of carbohydrate side chains and interactions within the cell membrane on the ability of CD44 to bind hyaluronan (Lesley et al., (1993) Adv. Immunol. 54, 271–335; Lokesh-war and Bourguignon, (1991) J. Biol. Chem. 266, 17983–17989) and on the specificity of GAG binding to CD44 (Chi-Rosso and Toole, (1987) J. Cell. Biochem. 33, 173–183).

Potential Role of a GAG-binding Protein in Cell Cycle Control

Cdc37 is an essential component of cell cycle regulation in yeast (Reed, (1980) Genetics 95, 561–577; Reed, (1992) Annu. Rev. Cell Biol. 8, 529–561; Ferguson et al., (1986) Nucl. Acids Res. 14, 6681–6697) and it may also play a role in certain differentiation events (Simon et al., (1991) Cell 67, 701–716; Cutforth and Rubin, (1994) Cell 77, 1027–1036). The biochemical function of cdc37 is unknown but genetic evidence strongly suggests that cdc37 influences the activity of p34$^{cdc2}$ kinase and consequently cell cycle progression (Reed, (1992) Annu. Rev. Cell Biol. 8, 529–561; Boschelli (1993) Mol. Cell. Biol. 13, 5112–5121; Cutforth and Rubin, (1994) Cell 77, 1027–1036). In this study it has been shown that a chick homologue of cdc37 exhibits characteristic properties of a GAG-binding protein. The putative GAG-binding regions of the chick cdc37 are well conserved in the Drosophila protein but only partially in yeast. Thus, considering the phylogenetic distance between these organisms, it seems reasonable to suppose that binding of GAGs to cdc37 may have a significant physiological role, at least in the metazoan species.

A great deal of evidence has been published indicating that GAGs are present, at least transiently, in the cytoplasm and in the nucleus. The types of GAGs shown to be present in these cellular compartments include hyaluronan, chondroitin sulfate, dermatan sulfate and heparan sulfate (Furukawa and Terayama, (1977) Biochim. Biophys. Acta 499, 278–280; Fedarko and Conrad, (1986) J. Cell Biol. 102, 587–599; Ishihara et al., (1986) J. Biol. Chem. 261, 13575–13580; Ripellino et al., (1988) J. Cell Biol. 106, 845–855; Ripellino et al., (1989) J. Cell Biol. 108, 1899–1907; Hiscock et al., (1994) J. Biol. Chem. 269, 4539–4546). Of particular interest is the observation that targeting of a specific sub-population of heparan sulfate to the nucleus of rat hepatoma cells increases markedly under conditions of reduced growth rate and decreases on stimulation of cell division (Ishihara and Conrad, (1989) J. Cell. Physiol. 138, 467–476; Fedarko et al., (1989) J. Cell. Physiol. 139, 287–294). It has also been shown that heparin and related polysaccharides inhibit the action of Fos and Jun on transcription events involved in cell cycle progression and evidence has been presented suggesting that endogenous nuclear heparan sulfate may exhibit this regulatory role in vivo (Busch et al., (1992) J. Cell Biol. 116, 31–42). Heparan sulfate/heparin is targeted to the nucleus and elicits similar effects to the above even when added extracellularly (Fedarko et al., (1989) J. Cell. Physiol. 139, 287–294; Pukac et al. (1990) Cell Regul. 1, 435–443). It seems likely then that GAGs in the cytoplasm or nucleus are involved in cell cycle regulation and possibly other intracellular events. Binding of GAG to cdc37 may mediate one or more of these events.

Example 2

Using the sequence information generated above in the chick system, a human cDNA library was probed. This human cDNA library screening yielded two full-length human isoforms encoding cdc37. These isoforms are shown in SEQ ID NO: 4 and SEQ ID NO: 6.

Example 3

The human cdc37 gene is highly homologous to that previously reported for the chicken gene. The homologies with the yeast gene are more limited, with some degree of conservation being observed in the N-terminal region of the yeast gene. The most striking divergence between the mammalian cdc37 and the Drosophila and yeast genes is the insertion of a region which appears to be a leucine zipper domain in the N-terminal portions of the protein. This part of the protein is predicted to be a coiled coil and is immediately preceded by a basic region with a structure homologous to other b-zip proteins. There is also a potential Rb-binding site in the protein. An alternately spliced version of the mRNA which is cloned, which, while producing a longer mRNA, produces a shorter protein. However, transfection of this cDNA into cells gives rise to two proteins of 35 and 54 kd. The 54 kD protein may result from a subsplice of the longer mRNA which potentially can encode a protein with a transmembrane-spanning region. Northern Blot analysis shows a near ubiquitous expression of the protein with varying ratios between at least the two alternately spliced forms. In adult tissues, there are high levels of expression of cdc37 in muscle.

Interestingly, the earliest actin G1-cyclin complex (that is, cyclin D/cdk4) does not efficiently form in mammalian cells or in vitro. Growth factors in mammalian cells appear to regulate the formation and activity of the cyclin D/cdk4 complex. It has been postulated that there may be "assembly factors" which are necessary for the formation of an active cyclin complex, but these have not been biochemically identified. The phenotype of observed cdc37 in yeast would be consistent with the idea that cdc37 may have a role to play in assembly of a cyclin/cdk4 complex.

To examine this possibility, we have looked for interactions between cdc37 and cyclin D and cdk4. HA-tagged cdc37 and HA-tagged cdk4 were transfected individually and together into cos1 cells. The cells were then labelled in the presence of 35S methionine and extracts of these cells were immunoprecipitated with either anti-HA antibody or anti-cdk4 antibody. Anti-HA antibody immunoprecipitates both cdc37 and the cdk4 tagged proteins, as expected. Antibody to cdk4 pulls down the expected cdk4 protein plus a protein that runs in the position of HA-cdc37. In cells that have been transfected only with cdk4 and not with cdc37, only the cdk4 band is observed. Addition of an ionic detergent SDS to these precipitates disrupts the association of the cdc37 band with cdk4. When a kinase inactive version of cdk4 is cotransfected with cdc37 and immunoprecipitated, the association with cdc37 is still observed. Thus, the association between cdk4 and cdc37 does not appear to require cdk4 kinase activity.

To determine whether this association could be observed in cells that were not overexpressing cdk4 and cdc37, extracts from several mammalian cell lines were precipitated with an antibody made against the chicken cdc37 and the resulting precipitates were analyzed by Western Blotting with an anti-cdk4 antibody. Material reacting to cdk4 was observed in all lanes where anti-cdc37 antibody was used but not where a pre-immune antiserum was used. This indicates that this interaction between cdk4 and cyclin D is occurring in vivo.

Thus, it has been found that the mammalian homologue of the yeast and Drosophila cdc37 gene products interacts with the mammalian G1 cyclin-dependent kinase cdk4 and with the heatshock protein hsp90. From GST binding data, it appears that all three of these proteins can be found in the same complex. These observations are consistent with the genetics of cdc37 in both yeast and Drosophila. In yeast, cdc37 mutations G1 arrest at the start point, and this phenotype appears to be due to a failure of the G1 cyclin CLN2 to associate with the cdc28 kinase. Thus yeast cdc37 appears to help the cyclin and cdc28 either associate of fold as a complex. The same may well be happening in mammalian cells as addition of cdc37 to cdk4 appears to enhance its ability to associate with cyclin D.

In Drosophila, cdc37 was isolated as an enhancer of the sevenless phenotype. In the same genetic screen, Drosophila hsp83, which is the homologue of the mammalian hsp90 proteins, was isolated. This observation suggests that, at least in Drosophila, cdc37 and the hsp90's are functionally involved in the same pathway. The data from mammalian cells indicate that there is a direct association between these proteins in mammalian cells and thus this would be consistent with findings of similar phenotypes of both genes in the Drosophila cells. Of course, the sevenless signalling pathway in Drosophila is equivalent to the mammalian ras-raf-map kinase pathway. Previous investigators have found that there is a 50 kilodalton protein associated with raf in mammalian cells as well as hsp90. The data reported herein suggest that this previously observed 50 kilodalton protein associated with raf is likely to be the mammalian cdc37 protein. Certainly cdc37 associates strongly with c-raf. In Drosophila, as well, cdc37 alleles can enhance the phenotype of cdc2 Drosophila mutations.

We claim:

1. An isolated nucleic acid molecule, or the complement thereof, the isolated nucleic acid molecule encoding the amino acid sequence shown in SEQ ID NO: 2.

2. An isolated nucleic acid molecule, or the complement thereof, the isolated nucleic acid molecule encoding the amino acid sequence shown in SEQ ID NO: 5.

3. A DNA expression construct comprising a nucleic acid molecule, or the complement thereof, the isolated nucleic acid molecule encoding the amino acid sequence shown in SEQ ID NO: 2.

4. A prokaryotic cell transformed with a DNA expression construct comprising a nucleic acid molecule, or the complement thereof, the isolated nucleic acid molecule encoding the amino acid sequence shown in SEQ ID NO: 2.

5. A eukaryotic cell transformed with a DNA expression construct comprising a nucleic acid molecule, or the complement thereof, the isolated nucleic acid molecule encoding the amino acid sequence shown in SEQ ID NO: 2.

6. A DNA expressionn construct comprising a nucleic acid molecule, or the complement thereof, the isolated nucleic acid molecule encoding the amino acid sequence shown in SEQ ID NO: 5.

7. A prokaryotic cell transformed with a DNA expression construct comprising a nucleic acid molecule, or the complement thereof, the isolated nucleic acid molecule encoding the amino acid sequence shown in SEQ ID NO: 5.

8. A eukaryotic cell transformed with a DNA expression construct comprising a nucleic acid molecule, or the complement thereof, the isolated nucleic acid molecule encoding the amino acid sequence shown in SEQ ID NO: 5.

\* \* \* \* \*

UNITED STATES PATENT AND TRADEMARK OFFICE
CERTIFICATE OF CORRECTION

PATENT NO. : 6,066,723
DATED : May 23, 2000
INVENTOR(S) : Grammatikakis et al.

It is certified that error appears in the above-indentified patent and that said Letters Patent is hereby corrected as shown below:

Column 1 after the title insert:

---This invention was made with government support under DE05838 and HD23681 awarded by the National Institutes of Health. The government has certain rights in the invention.---

Signed and Sealed this

Twenty-second Day of May, 2001

Attest:

NICHOLAS P. GODICI

*Attesting Officer*     Acting Director of the United States Patent and Trademark Office